United States Patent [19]
Bankert et al.

[11] Patent Number: 5,277,872
[45] Date of Patent: Jan. 11, 1994

[54] OPTICAL FIBER PH MICROSENSOR AND METHOD OF MANUFACTURE

[75] Inventors: Charles S. Bankert, Oceanside; Soonkap Hahn, Poway; Henry K. Hui, Laguna Niguel, all of Calif.

[73] Assignee: Puritan-Bennett Corporation, Carlsbad, Calif.

[21] Appl. No.: 902,402

[22] Filed: Jun. 19, 1992

Related U.S. Application Data

[63] Continuation of Ser. No. 598,137, Oct. 16, 1990, abandoned.

[51] Int. Cl.$^5$ .................. G01N 21/00; C09B 69/10
[52] U.S. Cl. ..................... 422/82.07; 422/82.06; 385/12; 128/634; 8/647
[58] Field of Search ............ 422/68.1, 82.06, 82.07, 422/82.08, 82.09; 436/68, 163, 165, 172; 128/634, 636; 356/39; 8/647; 385/12

[56] References Cited

U.S. PATENT DOCUMENTS

| Re. 31,879 | 5/1985 | Lubbers et al. | |
|---|---|---|---|
| 4,003,707 | 1/1977 | Lubbers et al. | 436/172 |
| 4,029,598 | 6/1977 | Neisios et al. | 252/408 |
| 4,194,877 | 3/1980 | Peterson | 8/526 |
| 4,200,110 | 4/1980 | Peterson et al. | 128/634 |
| 4,399,099 | 8/1983 | Buckles | 422/58 |
| 4,548,907 | 10/1985 | Seitz et al. | 436/163 |
| 4,560,248 | 12/1985 | Cramp et al. | 350/96.34 |
| 4,581,337 | 4/1986 | Frey et al. | 436/533 |
| 4,657,736 | 4/1987 | Marsoner et al. | 422/56 |
| 4,712,865 | 12/1987 | Hsu et al. | 350/96.29 |
| 4,785,814 | 11/1988 | Kane | 128/634 |
| 4,798,738 | 1/1989 | Yafuso et al. | 427/2 |
| 4,801,655 | 1/1989 | Murray, Jr. et al. | 525/369 |
| 4,803,049 | 2/1989 | Hirschfeld et al. | 422/58 |
| 4,842,783 | 6/1989 | Blaylock | 264/1.4 |
| 4,886,338 | 12/1989 | Yafuso et al. | 350/96.29 |
| 4,906,249 | 3/1990 | Fogt et al. | 8/647 |
| 4,925,268 | 5/1990 | Iyer et al. | 350/96.29 |
| 4,933,416 | 6/1990 | Gillis et al. | 528/74.5 |
| 4,999,306 | 3/1991 | Yafuso et al. | 436/68 |
| 5,015,843 | 5/1991 | Seitz et al. | 250/227.21 |
| 5,019,350 | 5/1991 | Rhum et al. | 422/82.07 |
| 5,081,041 | 1/1992 | Yafuso et al. | 436/68 |

FOREIGN PATENT DOCUMENTS

3343636A1 7/1984 Fed. Rep. of Germany.
WO 88/05533 7/1988 World Int. Prop. O. .

OTHER PUBLICATIONS

Thomas P. Jones and Marc D. Porter, "Optical pH Sensor Based on the Chemical Modification of a Porous Polymer Film", Anal. Chem. 1988, 60, 404-406.
Gehrich, et al., "Optical Fluorescence and Its Application to an Intravascular Blood Gas Monitoring System", *Transactions on Biomedical Engineering*, vol. BME-33, No. 2, Feb. 1986.
Munkholm et al., "Polymer Modification of Fiber Optic Chemical Sensors As a Method of Enhancing Fluorescence Signal for pH Measurement", Anal. Chem. 1986, 58, 1427-1430.
Offenbacher, et al. "Fluorescence Optical Sensors for Continuous Determination of Near-Neutral pH Values", Sensors and Actuators, 9 (1986) 73-84.
Peterson, et al. "Fiber Optic pH Probe for Physiological Use", Anal. Chem. 1980, 52, No. 6.
Zhujun, et al. "A Fluorescence Sensor for Quantifying pH in the Range from 6.5 to 8.5", Analytica Chimica Acta, 160, 1984, 47-55.
Saari, Linda, "pH Sensor Based on Immobilized Fluoresceinamine" Anal. Chem. 1982, 54, 821-823.
Zhujun et al. "Poly(Vinyl Alcohol) as a Substrate for Indicator Immobilization for Fiber-Optic Chemical Sensors" Anal. Chem. 1989, 61, 202-205.

*Primary Examiner*—Robert J. Warden
*Assistant Examiner*—T. A. Trembley
*Attorney, Agent, or Firm*—Fulwider Patton Lee & Utecht

[57] ABSTRACT

The optical fiber pH microsensor includes an optical fiber having a portion of the surface of a light conducting core covered with a layer of a pH sensitive dye material. The dye material is covalently bonded to a polymeric matrix which is in turn covalently bonded to the optical fiber core to prevent leaching of the indicator dye material during extended use. The dye material is crosslinked in situ over the tip of the optical fiber to yield a hydrophilic, ion permeable pH sensor which can be used intravascularly to monitor blood pH.

14 Claims, 1 Drawing Sheet

OPTICAL FIBER PH MICROSENSOR AND METHOD OF MANUFACTURE

This application is a continuation of application Ser. No. 07/598,137, filed Oct. 16, 1990, now abandoned.

BACKGROUND OF THE INVENTION

Field of the Invention

This invention is generally directed to chemical and biochemical quantitative analysis, and more specifically concerns an optical fiber sensor for measuring pH in a fluid or gaseous mixture.

Description of Related Art

In modern medicine, measurement of acidity (pH) in the blood has become an important factor in the determination of the respiratory status of a patient. Although electrodes have been developed which are capable of measuring pH in fluids, they are of limited use in measurement of in vivo blood pH levels. Optical sensors for taking intravascular measurements of acidity and other blood analytes such as oxygen and carbon dioxide show promise for in vivo measurement of blood pH. Such optical pH sensors typically include a fluorescent indicator dye, such as fluorescein or hydroxypyrenetrisulfonic acid (HPTS), placed over the tip of an optical fiber and a membrane cover over the dye which is permeable to the hydronium ions to be measured. The dye fluoresces when exposed to a certain wavelength of light conducted to it by the optical fiber. In practice, a pH sensor is fabricated by immobilizing a pH sensitive dye into a matrix attached to the distal end of the fiber. The dye is typically capable of existing in two forms, an anionic or base form, and a protonated or acid form. The two forms are each excited by a different frequency, but fluoresce at the same frequency, with the output responsive to excitation at the appropriate different frequencies being proportional to the pH of the sample to which the sensor is exposed. In this manner, measurement of the intensity of fluorescence of the indicator dye can be related to pH.

Optical absorbance indicator dyes, such as phenol red, have also been utilized in optical pH sensors. In this type of pH sensor, green and red light are emitted from one end of the optical fiber into the dye material, passing through the dye to be reflected back into another optical fiber. The green light is absorbed by the base form of the indicator, and the red light is not absorbed by the indicator, so that it may be used as an optical reference. The ratio of green to red light can thus be related to pH.

One approach to construction of optical fiber sensors involves the attachment of a dye filled porous glass to the tip of the optical fiber, such as by an adhesive. Another approach has involved the application of sensing material directly to the tip of the optical fiber. Another approach has involved the attachment of a sleeve which contains the dye indicator sensing material immobilized in a hydrophilic polymeric matrix by entrapment or by ionic interactions over the tip of the optical fiber. However, such sensors allow the indicator dye to leach out over extended time periods. Leaching of the indicator dye results in increasingly inaccurate blood pH measurements. Other covalently bonded sensors known in the art have either not been capable of attachment to the end of the optical fiber, or have been merely cast over the tip of the fiber without being crosslinked or covalently attached to the fiber.

There remains a need for a fiber optic pH sensor which provides covalent linkages between the dye and matrix, and between the matrix and the optical fiber, to prevent leaching of the indicator material during periods of extended use of the sensor in measuring blood pH intravascularly. It would also be desirable to allow for control of the concentration of dye in the final sensor matrix, and to allow for uniform application of the sensor matrix over a wide range of sensor thicknesses.

SUMMARY OF THE INVENTION

Briefly and in general terms, the present invention provides a new and improved optical fiber pH microsensor which includes a pH sensitive dye material covalently bonded to a polymeric matrix, which is in turn covalently bonded to the surface of the core of the optical fiber to prevent leaching of the indicator dye material during extended use. The dye material is crosslinked in situ over the tip of the optical fiber to yield a hydrophilic, ion permeable pH sensor which can be used intravascularly to monitor blood pH.

Because the dye is attached to a stable polymer which is completely miscible with the crosslinking component, the exact concentration of the dye in the final sensor material can be quantified and closely controlled by use of the invention. Control of the viscosity and dilution of the polymer and choices of the solvents used, including various combinations of co-solvents, allow for uniform application of the sensor material over a wide range of thicknesses of the sensor. The nature of the crosslinking polymer also allows for formation of the sensor with a closed cell polymer or an open cell material, so that the response time and molecular exclusion parameters of the sensor may be suitably adjusted.

Other aspects and advantages of the invention will become apparent from the following detailed description and the accompanying drawings, which illustrate, by way of example, the features of the invention.

DESCRIPTION OF THE PREFERRED EMBODIMENT

The extensive application of long term intravascular blood pH sensors utilizing fluorescent dyes immobilized on the distal ends of optical fibers has been limited by a number of problems. Among the problems is the leaching of dye indicator materials inadequately immobilized in the chemical sensing area of optical fiber pH sensors during extended periods of monitoring of blood pH levels. This has resulted in inaccurate long term intravascular measurement of blood pH by this method. According to the present invention, an optical fiber pH microsensor is prepared by covalently bonding the dye material to the polymeric matrix, and covalently bonding the crosslinked polymer to the tip of the optical fiber.

Figure 1:
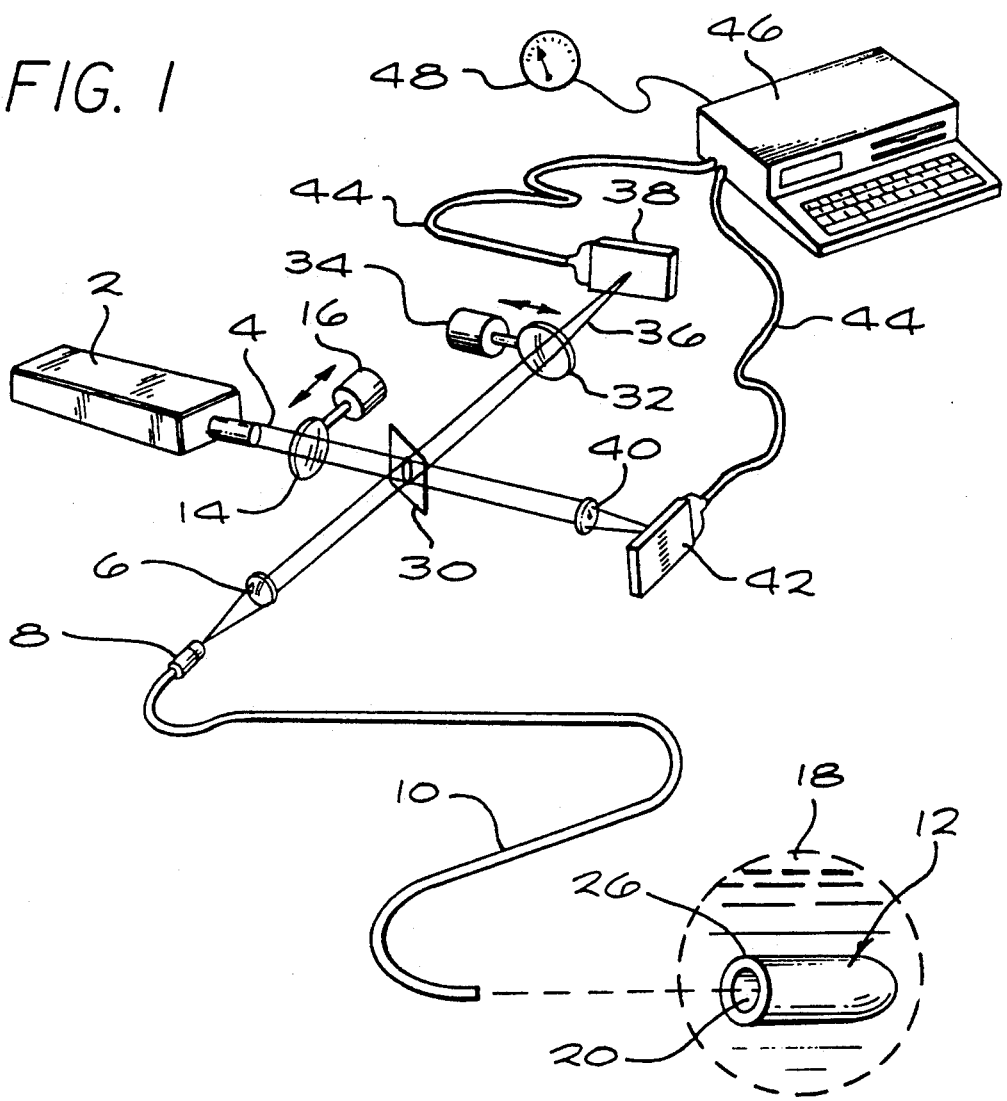
FIG. 1 is a perspective diagram of a fiber optic sensor system utilizing the sensor of the invention for monitoring blood pH levels.

As is shown in the drawings, which are provided for purposes of illustration, the invention is embodied in an optical fiber pH microsensor which may be used for intravascular monitoring of blood pH levels, and a method for making the pH microsensor. As is illustrated in FIG. 1, in such a system a light source 2 provides an output light beam 4 that is passed through a dichroic mirror 30 and focused by a lens system 6 into a connector 8 of an optical fiber 10, which carries the light beam to a sensor module 12 at a distal end of the optical fiber. The light source preferably includes one or more excitation filters 14, actuated and controlled by stepper motor 16, for controlling the wavelength range of the light provided to the sensor module. Sensor module 12 is adapted to be placed in a fluid 18, such as blood, for fluid, such as pH. The sensor could, of course, be adapted to detect concentrations of gases, such as oxygen or carbon dioxide, drugs, or other blood constituents.

Figure 2:
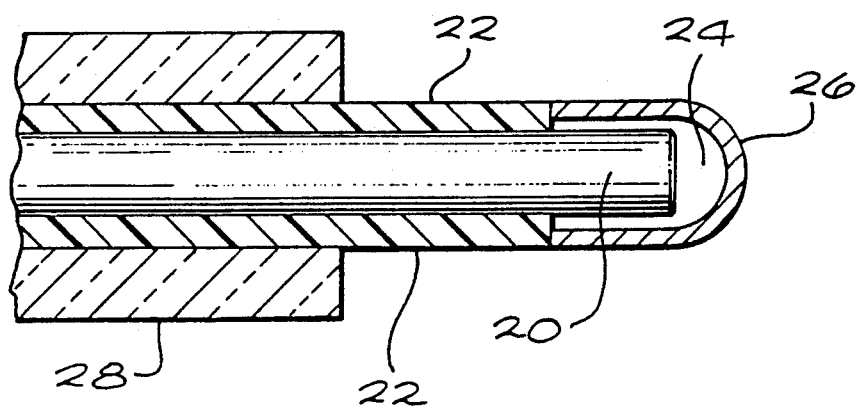
FIG. 2 is an enlarged, cross-sectional schematic diagram of the fiber optic sensor.

As is illustrated in FIG. 2, the optical fiber sensor module is generally formed from an optical fiber having a light conducting core 20, such as glass, and an outer cladding material 22 having a refractive index such that light conducted by the core is substantially retained in the core material. A length of cladding on the distal end of the optical fiber is removed, leaving an exposed distal tip of the core. The exposed distal tip, preferably primed to provide sites for covalent attachment of a polymeric matrix, is coated with the polymeric matrix 24, which is preferably a hydrophilic polymer covalently bonded to one or more indicator dyes which are known to fluoresce in response to irradiation with light of various wavelength ranges. The polymeric matrix is preferably a polyether polyisocyanate, such as HYPOL-2002 made by W. R. Grace & Co., covalently bonded in a polyether polyamine form to HPTS.

A coat of reflective material 26 is also preferably provided over the dye containing sensing matrix, to retain and reflect both the irradiating light and the fluorescence emissions from the dye indicator. The reflective coating is preferably a mixture of about 50% by weight titanium dioxide in a polyether polyisocyanate, such as HYPOL-2002 diluted to 37% in acetone. Ten percent water by weight is utilized to initiate crosslinking. In certain applications, an exterior coating or sheath 28 may be used to further facilitate or protect the optical fiber assembly.

The output optical fiber 10 may also carry light fluoresced from the dye indicators via a dichroic mirror 30 to emission filters 32 which may be actuated by stepper motor 34 and the fluorescent light beam 36 upon a detector array 38. Similarly, the portion of the light beam 4 that passes through the dichroic mirror 30 may be focused by a suitable lens 40 upon a reference detector array 42, which allows measurement of the excitation signal strength. The electrical output of the detectors is fed through cables 44 to a computer 46, such as an IBM PC, which receives the electrical output of the detectors and determines the blood analyte being monitored, such as pH. The computer is preferably programmed to determine the pH based upon the specific measurement of fluorescence intensity represented by the electrical output signal received by the computer, according to an algorithm based upon signal outputs from measurements from samples with known pH levels. The output of the computer may be indicated on a meter 48 or another suitable readout device.

The method of making the optical fiber pH microsensor involves hydrolyzing the hydrophilic polymer, which is preferably a polyether polyisocyanate, such as HYPOL-2002, preferably in the presence of an alkaline base and butanone, to form the polyether polyamine, HYPOL-polyamine, and carbon dioxide gas, as shown in equation (I) below:

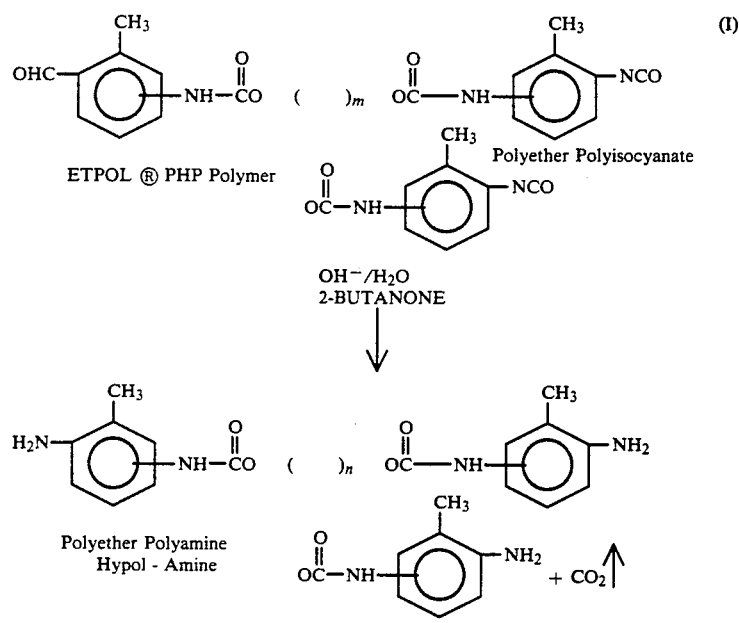

The HYPOL-polyamine is then reacted with an sulfonyl chloride form of the indicator dye, preferably acetoxy-HPTS-SO2Cl to covalently bond the dye to the HYPOL-polyamine, forming HYPOL-polyamine-HPTS, as shown in equation (II) below:

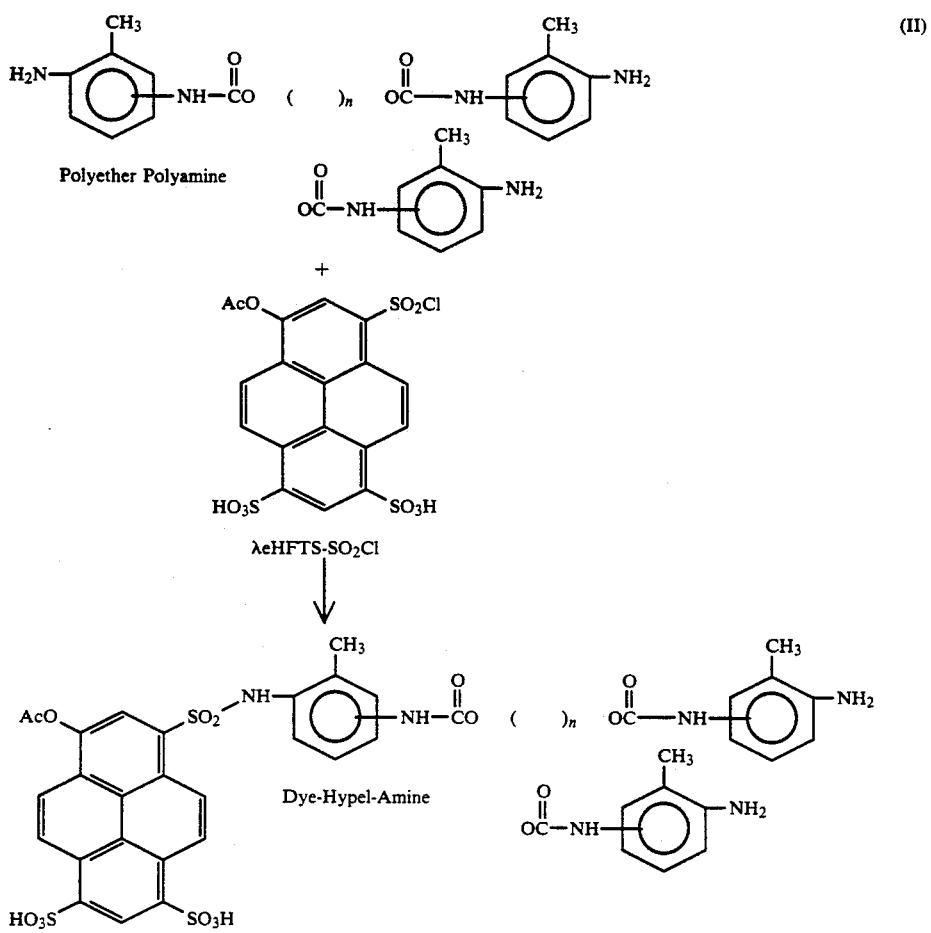

(II)

facilitating uniform application of the sensor material over a wide range of thicknesses of the sensor.

In order to prepare an optical fiber for application of the dye sensor material, a portion of the cladding at the end of the optical fiber is removed to expose the glass core. The exposed surface of the glass core is primed by treating it with an isocyanatosilane, for example, isocyanatopropyltriethoxysilane, to provide sites for covalent attachment of the polymer to the fiber. The HYPOL-polyamine-HPTS is diluted with HYPOL-2002 and a common solvent such as acetone, as desired, to form a dye mixture, ready for application to the optical fiber, that is stable for several days if stored under anhydrous conditions. By controlling the viscosity of the uncured polymer matrix material, a desired thickness of matrix material may be applied. In practice, it has been found that a variety of solvents of the matrix may be used to alter both the thickness of the matrix applied and the cured properties of the matrix. For example, acetone, methanol, or ethanol may be used in greater proportions as a solvent if relatively thin coatings are desired, while polyvinylpyrrolidone in DMI may be used in greater proportions for thicker coatings. Similarly, glycerol, polyols, and hydroxyethyl methacrylate may be used as a matrix modifier in various proportions to alter the resilience and strength of the cured matrix.

When it is desired to apply the dye mixture to the exposed surface of the glass core of the optical fiber, the HYPOL-2002/HYPOL-polyamine-HPTS solvent mixture is mixed with approximately 10% water by weight to initiate cross-linking, and the mixture is then applied to the exposed tip of the fiber. The applied mixture is then allowed to cure at room temperature for approximately one hour to form the pH sensing matrix, as shown in Equation III below:

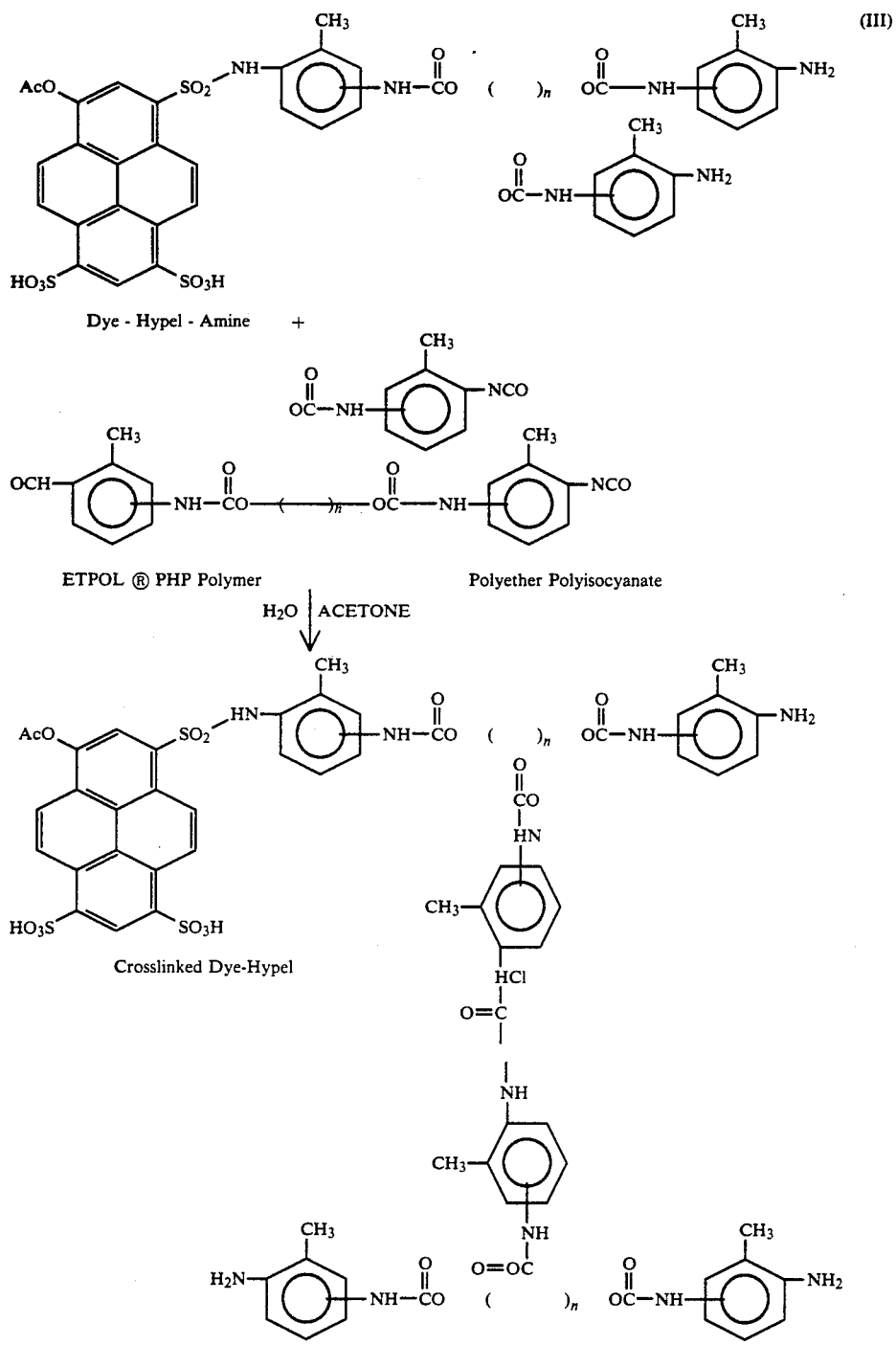

After the sensing matrix is completely solidified, the coating of reflective material 26 may be applied over the sensing matrix. The cured dye sensor matrix is preferably coated with a reflective material comprising approximately 50% $TiO_2$ in HYPOL-2002, which serves to provide protection, optical isolation and reflection of both the excitation and fluorescence emission light.

From the foregoing it will be appreciated that the invention provides an optical fiber pH microsensor which will prevent the problems of leaching of dye indicator materials during extended periods of intravascular monitoring of blood pH. It is significant that the optical fiber microsensor is prepared by covalently bonding the dye material to the polymeric matrix, and covalently bonding the crosslinked polymer to the tip of the optical fiber. As will be readily appreciated, the principles of the invention are applicable to other types of optical fiber microsensors such as blood oxygen and carbon dioxide sensors, in which similar problems of inaccuracies of analyte measurements have resulted from the leaching of dye indicator materials during extended periods of use of the sensors, particularly in intravascular monitoring of blood analytes.

While particular forms of invention have been illustrated and described, it will be apparent that various modifications can be made without departing from the spirit and scope of this invention. Accordingly, it is not intended that the invention be limited, except as by the appended claims.

What is claimed is:

1. An analyte sensor, comprising:
   a light conducting optical fiber having an outer surface;
   an isocyanatosilane primer compound covalently bonded to said outer surface of said light conducting optical fiber;
   an analyte sensing matrix crosslinked in situ on the surface of the light conducting optical fiber, the analyte sensing matrix including a polyether polyamine polymer and a fluorescent dye indicator material covalently bonded to said polyether polyamine polymer, with said polymer polyamine polymer covalently bonded to said isocyanatosilane primer compound covalently bonded to said outer surface of said light conducting optical fiber.

2. The sensor of claim 1, further including a coating of reflective material applied over the analyte sensing matrix.

3. The sensor of claim 1, wherein said fluorescent dye indicator material comprises hydroxypyrenetrisulfonic acid.

4. A microsensor for measuring pH in a fluid, comprising:
   a sensor member including a light transmitting optical fiber having a bonding surface;
   an isocyanatosilane primer compound covalently bonded to said bonding surface of said light transmitting optical fiber;
   a pH sensing matrix crosslinked in situ on the bonding surface of the light transmitting optical fiber for receiving an excitation light signal transmitted by said light transmitting optical fiber, the pH sensing matrix including a fluorescent dye indicator material for emitting an output light signal carried by said light transmitting optical fiber, said fluorescent dye indicator material being covalently bonded to a polyether polyamine and a polyether polyisocyanate crosslinked to said polyether polyamine, said polyether polyamine being covalently bonded to said isocyanatosilane primer compound on said bonding surface of said light transmitting optical fiber; and
   a coating of reflective material applied over the pH sensing matrix.

5. The microsensor of claim 4, wherein said coating of reflective material comprises titanium dioxide.

6. The microsensor of claim 4, wherein said fluorescent dye indicator material comprises hydroxypyrenetrisulfonic acid.

7. The microsensor of claim 4, wherein said coating of reflective material comprises a mixture of approximately 50% titanium dioxide with the remainder comprising polyether polyisocyanate.

8. A method of making an analyte sensor, comprising the steps of:
   covalently bonding an isocyanatosilane primer compound to a portion of a surface of a light conducting optical fiber to provide sites for covalent bonding;
   covalently bonding a fluorescent dye indicator material to a polyether polyamine; and
   crosslinking said polyether amine which is covalently bonded to said fluorescent dye indicator material to a polyether polyisocyanate in situ on the surface of the light conducting optical fiber to form an analyte sensing polymeric matrix and to covalently bond said analyte sensing polymeric matrix to said isocyanatosilane primer compound covalently bonded to said portion of the surface of said light conducting optical fiber.

9. The method of claim 8, wherein said light conducting optical fiber includes a glass light conducting inner core, and said isocyanatosilane primer compound is applied to a portion of the surface of the glass light conducting inner core.

10. The method of claim 8, further including the step of applying a coating of reflective material over the analyte sensing polymeric matrix.

11. The method of claim 8, wherein said isocyanatosilane primer compound is isocyanatopropyltriethoxysilane.

12. A method of making a microsensor for measuring a pH in a fluid, comprising the steps of:
   covalently bonding an isocyanatosilane primer compound to a glass portion of a light conducting optical fiber to provide sites for covalent bonding;
   hydrolyzing a polyether polyisocyanate to produce a polyether polyamine;
   covalently bonding a fluorescent dye indicator to said polyether polyamine to produce a fluorescent dye polymer;
   diluting said fluorescent dye polymer with a diluent comprising polyether polyisocyanate;
   mixing said fluorescent dye polymer and polyether polyisocyanate with approximately 10 percent water by weight to initiate crosslinking between said fluorescent dye polymer and said polyether polyisocyanate to form a pH sensing matrix; and
   applying said mixture of fluorescent dye polymer and polyether polyisocyanate in which crosslinking has been initiated to said glass portion of said light conducting optical fiber, and allowing said mixture to cure to form a covalent bond between said polyether polyamine in said pH sensing matrix and the isocyanatosilane primer compound covalently bonded to the glass portion.

13. The method of claim 12, further including the step of applying a coating of a mixture comprising approximately 50 percent titanium dioxide with the remainder comprising polyether polyisocyanate to provide a layer of reflective material over the pH sensing matrix.

14. The method of claim 12, wherein said fluorescent dye indicator comprises hydroxypyrenetrisulfonic acid.

* * * * *

UNITED STATES PATENT AND TRADEMARK OFFICE
CERTIFICATE OF CORRECTION

PATENT NO. : 5,277,872
DATED : January 11, 1994
INVENTOR(S) : Charles S. Bankert, Soonkap Hahn, Henry K. Hui It is certified that error appears in the above-indentified patent and that said Letters Patent is hereby corrected as shown below:

Column 3, line 11, after "such as blood for" insert --quantitative measurement of a chemical parameter of the--.

Column 4, line 39, in the equation change "$(\quad)_m$" to --$(\quad)_n$--.

Column 4, line 42, in the description located under the equation change "EITPOL® PHP Polymer" to --HYPOL® PHP Polymer--.

Column 5, line 23, change equation above the arrow from "$\lambda$eHPTS-SO$_2$Cl" to --AcHPTS-SO$_2$Cl--.

Column 9, line 19, change "with said polymer polyamine" to --with said polyether polyamine--.

Column 10, line 29 and line 30, change "for measuring a pH in a fluid," to --for measuring pH in a fluid--.

Signed and Sealed this

Twenty-eighth Day of May, 1996

*Attest:*

BRUCE LEHMAN

*Attesting Officer*   *Commissioner of Patents and Trademarks*